United States Patent
Reuter et al.

(10) Patent No.: US 6,891,016 B2
(45) Date of Patent: May 10, 2005

(54) ALKYLENEDIOXYTHIOPHENE DIMERS AND TRIMERS

(75) Inventors: Knud Reuter, Krefeld (DE); Valery A. Nikanorov, Moskau (RU); Vassily M. Bazhenov, Mosaku (RU)

(73) Assignee: H. C. Starck GmbH, Goslar (DE)

( * ) Notice: Subject to any disclaimer, the term of this patent is extended or adjusted under 35 U.S.C. 154(b) by 0 days.

(21) Appl. No.: 10/603,844

(22) Filed: Jun. 25, 2003

(65) Prior Publication Data

US 2004/0031951 A1 Feb. 19, 2004

(30) Foreign Application Priority Data

Jun. 28, 2002 (DE) .......................... 102 29 218

(51) Int. Cl.$^7$ .............................................. C08G 75/00
(52) U.S. Cl. ........................ 528/373; 528/377; 528/383; 528/425; 528/480; 528/486
(58) Field of Search ................................. 528/373, 377, 528/383, 425, 480, 486

(56) References Cited

U.S. PATENT DOCUMENTS

| | | | |
|---|---|---|---|
| 4,959,430 A | 9/1990 | Jonas et al. | 526/257 |
| 4,987,042 A | 1/1991 | Jonas et al. | 429/213 |
| 5,035,926 A | 7/1991 | Jonas et al. | 427/393.1 |

OTHER PUBLICATIONS

Sankaran et al.; " High contrast electrochromic polymers from alkyl–derivatized poly (3,4–ethylenedioxythiophenes)" Macromolecules, vol. 30, 2582–2588 (1997).*

Adv. Mater. 12, No. 7, month unavailable (2000) p. 481–494, L. Groenendaal, F. Jonas, D. Freitag, H. Pielartzik & J.R. Reynolds, Poly(3,4–ethylenedioxythiophene) and Its Derivatives: Past, Present, and Future.

Advances in Physical Organic Chemistry, 9, p. 1–24, "Superacid Systems", R.J. Gillespie, and T.E. Peel.

Chem. Rev. month unavailable 1982, 82, p. 591–614 "Thermodynamic Behavior of Alkanes In Superacid Media" P–L. Fabre, J. Devynck, and B. Tremillon.

Angewandte Chemi, vol. 12, No. 3, Mar. 1973, pp. 173–212, G.A. Olah, "Carbocations and Electrophilic Reactions".

Curr. Chem. 80, p. 9–88, month unavailable 1979, G.A. Olah, "From Boron Trifluoride to Antimony Pentafluoride in Search of Stable Carbocatins".

Tetrahedron 55 month unavailable (1999) p. 11745–11745, A.K. Mohanakrishnan, A. Hucke, M. Lynon, M. V. Lakshmikantham and M.P. Cava**, "Functionalization of 3,4–Ethylenedioxythiophene".

* cited by examiner

Primary Examiner—Duc Truong
(74) Attorney, Agent, or Firm—Joseph C. Gil; James R. Franks

(57) ABSTRACT

The invention relates to novel 3,4-alkylenedioxythiophene dimers and trimers, to their preparation and to their use as precursors for conductive polymers.

15 Claims, No Drawings

ALKYLENEDIOXYTHIOPHENE DIMERS AND TRIMERS

CROSS REFERENCE TO RELATED PATENT APPLICATION

The present patent application claims the right of priority under 35 U.S.C. 119 (a)–(d) of German Patent Application No. 102 29 218.3, filed Jun. 28, 2002.

FIELD OF THE INVENTION

The invention relates to novel 3,4-alkylenedioxythiophene dimers and trimers, to their preparation and to their use as precursors for conductive polymers.

BACKGROUND OF THE INVENTION

The class of π-conjugated polymeric compounds (also referred to as conductive polymers or as synthetic metals) has been the subject-matter of numerous publications in the last few decades.

Owing to the considerable delocalization of the π-electrons along the main chain, these polymers exhibit interesting (non-linear) optical properties, and, after oxidation or reduction, are good electrical conductors. These compounds will therefore probably take on a leading and active role in various practical fields of application, for example in data storage, optical signal processing, suppression of electromagnetic interference (EMI) and solar energy conversion, and also in rechargeable batteries, light-emitting diodes, field-effect transistors, circuit boards, sensors and antistatic materials.

Examples of known π-conjugated polymers include polypyrroles, polythiophenes, polyanilines, polyacetylenes, polyphenylenes and poly(p-phenylenevinylenes). A particularly important and industrially utilized polythiophene is poly(ethylene-3,4-dioxythiophene), which exhibits high conductivity in its oxidized form and is described, for example, in EP 339 340 A2. An overview of numerous poly(alkylene-3,4-dioxythiophene) derivatives, in particular poly(ethylene-3,4-dioxythiophene) derivatives, their monomers, syntheses and applications, is given by L. Groenendaal, F. Jonas, D. Freitag, H. Pielartzik & J. R. Reynolds, Adv. Mater. 12, (2000) p. 481–494.

To achieve very high conductivities, there is employed in situ polymerization methodology, in which the monomeric ethylene-3,4-dioxythiophene is reacted with oxidizing agents, for example iron-III tosylate, in solution to give a highly conductive layer of oxidized poly(ethylene-3,4-dioxythiophene). This procedure is utilized, for example, for producing capacitors.

Although there is thus a variety of very suitable techniques for preparing conductive poly(ethylene-3,4-dioxythiophene)s, there is a need for further improvements. In particular, routes and intermediates are sought which facilitate very rapid formation of conductive poly(ethylene-3,4-dioxythiophene)s.

This need is met by providing novel, optionally substituted 3,4-alkylenedioxythiophene dimers and trimers.

SUMMARY OF THE INVENTION

The present invention thus provides compounds of the general formula I

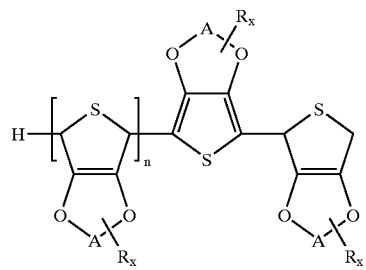

where

A is an optionally substituted $C_1$–$C_4$-alkylene radical, preferably an optionally substituted $C_2$–$C_3$-alkylene radical, R is one or more identical or different, linear or branched, optionally substituted $C_1$–$C_{18}$-alkyl radical(s), preferably a linear or branched, optionally substituted $C_1$–$C_{14}$-alkyl radical(s), optionally substituted $C_5$–$C_{12}$-cycloalkyl radical(s), optionally substituted $C_6$–$C_{14}$-aryl radical(s), optionally substituted $C_1$–$C_4$-hydroxyalkyl radical(s), preferably optionally substituted $C_1$–$C_2$-hydroxyalkyl radical(s) or one or more hydroxyl radical(s), x is an integer from 0 to 8, preferably from 0 to 6, more preferably 0 or 1, and n is 0 or 1.

For the purposes of the invention, formula I should be interpreted in such a way that the A radical is optionally substituted at any desired number of points x by x R radicals, and two R radicals in each case on the same carbon atom of A may be joined.

The invention likewise provides mixtures of compounds of the general formula I which may be of compounds having different R radicals, different numbers x of the R radicals and also different n.

DETAILED DESCRIPTION OF THE INVENTION

The invention preferably provides compounds of the general formulae I-a or I-b,

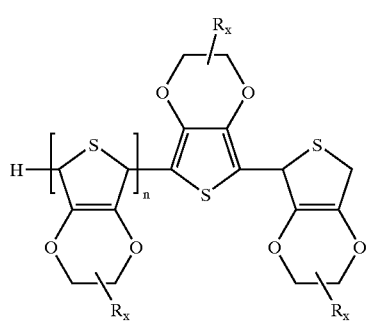

(I-b)

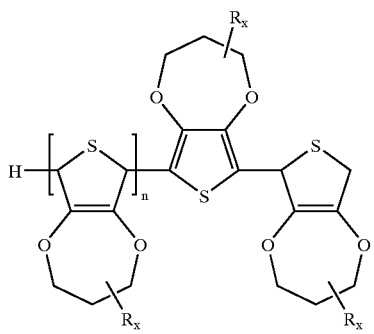

where
- R is one or more identical or different, linear or branched, optionally substituted $C_1$–$C_{18}$-alkyl radical(s), preferably a linear or branched, optionally substituted $C_1$–$C_{14}$-alkyl radical(s), optionally substituted $C_5$–$C_{12}$-cycloalkyl radical(s), optionally substituted $C_6$–$C_{14}$-aryl radical(s), optionally substituted $C_1$–$C_4$-hydroxyalkyl radical(s), preferably optionally substituted $C_1$–$C_2$-hydroxyalkyl radical(s) or one or more hydroxyl radical(s),
- x is an integer from 0 to 8, preferably from 0 to 6, more preferably 0 or 1, and
- n is 0 or 1.

These compounds are more preferably of the general formulae I-a-1 or I-b-1, (I-a-1)

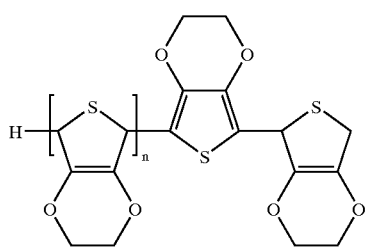

(I-b-1)

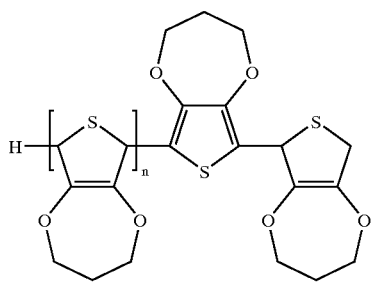

where
n is 0 or 1.

In a preferred embodiment, the compounds are dimeric compounds of the formulae I-a-1a or I-a-2a, (I-a-1a)

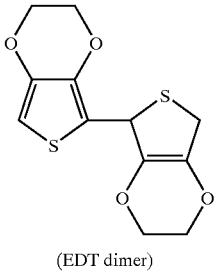

(EDT dimer)

(I-a-2a)

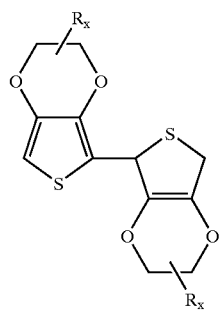

where

- R is one or more identical or different, linear or branched, optionally substituted $C_1$–$C_{18}$-alkyl radical(s), preferably a linear or branched, optionally substituted $C_1$–$C_{14}$-alkyl radical(s), optionally substituted $C_5$–$C_{12}$-cycloalkyl radical(s), optionally substituted $C_6$–$C_{14}$-aryl radical(s), optionally substituted $C_1$–$C_4$-hydroxyalkyl radical(s), preferably optionally substituted $C_1$–$C_2$-hydroxyalkyl radical(s) or one or more hydroxyl radical(s), and
- x is an integer from 0 to 8, preferably from 0 to 6, more preferably 0 or 1, optionally in a mixture with monomeric reactants.

In a further preferred embodiment, compounds are trimeric compounds of the formulae Formula I-a-1b and I-a-2b, (I-a-1b)

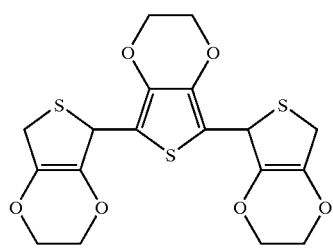

(EDT trimer)

(I-a-2b)

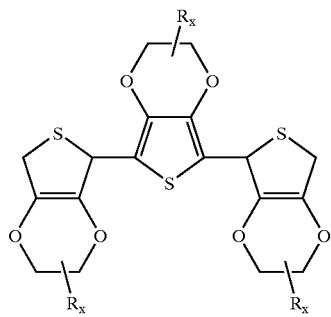

where
- R is one or more identical or different, linear or branched, optionally substituted $C_1$–$C_{18}$-alkyl radical(s), preferably a linear or branched, optionally substituted $C_1$–$C_{14}$-alkyl radical(s), optionally substituted $C_5$–$C_{12}$-cycloalkyl radical(s), optionally substituted $C_6$–$C_{14}$-aryl radical(s), optionally substituted $C_1$–$C_4$-hydroxyalkyl radical(s), preferably optionally substituted $C_1$–$C_2$-hydroxyalkyl radical(s) or one or more hydroxyl radical(s), and
- x is an integer from 0 to 8, preferably from 0 to 6, more preferably 0 or 1, optionally in a mixture with monomeric reactants and/or the above-described dimeric products of the formulae I-a-1a and/or I-a-2a.

In a further preferred embodiment, the compounds are dimeric compounds of the formulae I-b-1a and I-b-2a, (I-b-1a)

(I-b-2a)

where
- R is one or more identical or different, linear or branched, optionally substituted $C_1$–$C_{18}$-alkyl radical(s), preferably a linear or branched, optionally substituted $C_1$–$C_{14}$-alkyl radical(s), optionally substituted $C_5$–$C_{12}$-cycloalkyl radical(s), optionally substituted $C_6$–$C_{14}$-aryl radical(s), optionally substituted $C_1$–$C_4$-hydroxyalkyl radical(s), preferably optionally substituted $C_1$–$C_2$-hydroxyalkyl radical(s) or one or more hydroxyl radical(s), and
- x is an integer from 0 to 8, preferably from 0 to 6, more preferably 0 or 1, optionally in a mixture with monomeric reactants.

In a further preferred embodiment, the compounds are trimeric compounds of the formulae I-b-1b and I-b-2b, (I-b-1b)

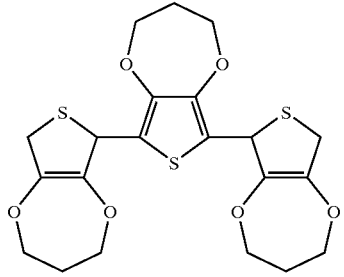

(I-b-2b)

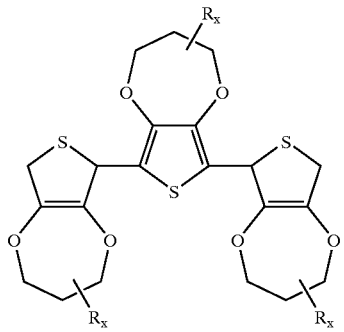

where
- R is one or more identical or different, linear or branched, optionally substituted $C_1$–$C_{18}$-alkyl radical(s), preferably a linear or branched, optionally substituted $C_1$–$C_{14}$-alkyl radical(s), optionally substituted $C_5$–$C_{12}$-cycloalkyl radical(s), optionally substituted $C_6$–$C_{14}$-aryl radical(s), optionally substituted $C_1$–$C_4$-hydroxyalkyl radical(s), preferably optionally substituted $C_1$–$C_2$-hydroxyalkyl radical(s) or one or more hydroxyl radical(s), and
- x is an integer from 0 to 8, preferably from 0 to 6, more preferably 0 or 1, optionally in a mixture with monomeric reactants and/or above-described dimeric products of the formula I-b-1a and/or I-b-2a.

For the purposes of the invention, $C_1$–$C_{14}$-alkylene radicals A are methylene, ethylene, n-propylene or n-butylene. For the purposes of the invention, examples of linear or branched $C_1$–$C_{14}$-alkyl radicals include methyl, ethyl, n- or isopropyl, n-, iso-, sec- or tert-butyl, n-pentyl, 1-methylbutyl, 2-methylbutyl, 3-methylbutyl, 1-ethylpropyl, 1,1-dimethylpropyl, 1,2-dimethylpropyl, 2,2-dimethylpropyl, n-hexyl, n-heptyl, n-octyl, 2-ethylhexyl, n-nonyl, n-decyl, n-undecyl, n-dodecyl, n-tridecyl and n-tetradecyl, and of $C_1$–$C_{18}$-alkyl radicals also n-hexadecyl or n-octadecyl, examples of $C_5$–$C_{12}$-cycloalkyl radicals include cyclopentyl, cyclohexyl, cycloheptyl, cyclooctyl, cyclononyl or cyclodecyl, examples of $C_6$–$C_{14}$-aryl radicals include phenyl, o-, m- and p-tolyl, benzyl, 2,3-, 2,4-, 2,5-, 2,6-, 3,4-, 3,5-xylyl, mesityl and naphthyl, and examples of $C_1$–$C_4$-hydroxyalkyl radicals include hydroxymethyl, 1-hydroxyethyl, 2-hydroxyethyl, 1-hydroxypropyl, 2-hydroxypropyl, 3-hydroxypropyl, 1-hydroxybutyl, 2-hydroxybutyl, 3-hydroxybutyl and 4-hydroxybutyl. The above listing serves to illustrate the invention by way of example and should not be regarded as exclusive.

Useful substituents of the above mentioned radicals include numerous organic groups, halogen, in particular fluorine, chlorine or bromine, and also ether, thioether, disulphide, sulphoxide, sulphone, aldehyde, keto, carboxylic ester, carbonate, cyano, alkylsilane and alkoxysilane groups and/or carboxylamide groups.

Surprisingly, the compounds according to the invention are prepared in a simple manner by reacting compounds or mixtures of compounds of the general formula II

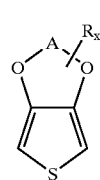

(II)

with each other in the presence of a Lewis acid and/or a protic acid as catalyst.

The invention therefore also provides a process for preparing compounds of the general formula I

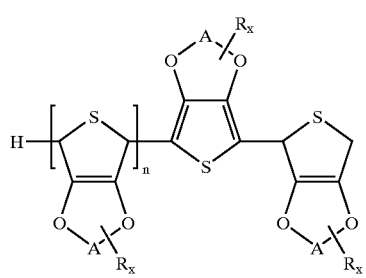

(I)

where
A, R, x and n are each as defined in the general formula I, characterized in that compounds of the general formula II

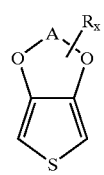

(II)

where
A, R and x are each as defined in the general formula I are reacted with each other in the presence of Lewis acids and/or protic acids as catalysts.

The practice of the process according to the invention may also result in mixtures of the monomeric compounds of the general formula II with the compounds of the general formula I according to the invention which likewise form part of the subject-matter of the invention. These may possibly also be isomeric mixtures, racemates or else pure isomers of the compounds according to the invention, optionally in a mixture with the monomeric compounds of the formula II. These mixtures may be purified with the aid of customary separating processes, for example by column chromatography or fractional crystallization or else distillation. Preference is given to applying column chromatography separation on silica gel and subsequent fractional crystallization in the separation of reactant/product and isomer mixtures of the compounds according to the invention. Examples of useful eluents for column chromatography separation include halogenated aliphatic hydrocarbons, for example methylene chloride, chloroform and also mixtures of these, preferably methylene chloride.

In preferred embodiments of the process according to the invention, the compounds of the formula II are the monomeric compounds II-a to II-d or mixtures thereof

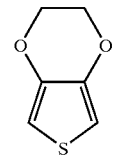

(II-a)

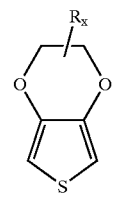

(II-b)

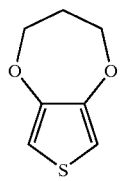

(II-c)

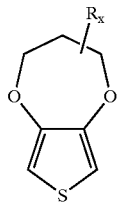

(II-d)

where R and x are as defined above.

In a preferred embodiment, preference is given to carrying out the process according to the invention to prepare compounds of the general formula I in the presence of Lewis acids, more preferably non-oxidizing Lewis acids, as catalysts.

Preferred Lewis acids which are used as catalysts in the process according to the invention include boron trihalides and aluminium trihalides, phosphorus trihalides, titanium tetrahalides or zirconium tetrahalides, tin(IV) halides, arsenic halides and antimony halides, tantalum pentahalides and zinc halides, especially preferably boron trifluoride, antimony pentachloride, aluminium trichloride, titanium tetrachloride, tin tetrachloride and zinc chloride. Very particular preference is given to using boron trifluoride (for example in the form of the etherate or another $BF_3$ complex, for example with tetrahydrofuran), antimony pentachloride, tin tetrachloride and titanium tetrachloride.

In a further preferred embodiment, the process according to the invention is carried out to prepare compounds of the general formula I in the presence of protic acids as catalysts.

Preferred protic acids which may be used as catalysts in the process according to the invention include sulphonic acids such as benzenesulphonic acid, p-toluenesulphonic acid, methanesulphonic acid, camphorsulphonic acid and poly(styrenesulphonic acid), carboxylic acids, such as trifluoroacetic acid and trichloroacetic acid, inorganic acids such as HCl, sulphuric acid and phosphoric acid, and superacids. Superacids are those protic acids whose acidity is greater than that of 100% sulphuric acid (Gillespie, Adv. Phys. Org. Chem. 9, 1–24 (1972)). Such acids are disclosed, for example, in P.-L- Fabre, J. Devynck and B. Trémillon, Chem. Rev. 82, 591–614 (1982), in G. A. Olah, Angew. Chem. 85, 183–225 (1973) or in G. A. Olah, Top. Curr. Chem. 80, 19–88 (1979). Examples of superacids include "magic acid" $FSO_3H.SbF_5$, $FSO_3H.SbF_5.SO_2$, $HSbF_6$, $HBF_4$, $H[B(OSO_3H)]_4$, $HTaF_6$, $HF.SnCl_4$.

Particular preference is given to using protic acids selected from the group of sulphonic acids, carboxylic acids and superacids, and very particular preference is given to using p-toluenesulphonic acid, methanesulphonic acid, camphor-10-sulphonic acid or trifluoroacetic acid as the catalyst in the process according to the invention.

The amounts of Lewis acids and protic acids used in the process according to the invention are between 0.01 and 100% by weight of acid, based on the thiophene monomer to be di- and trimerized. The amounts of Lewis acids are generally in the lower percent by weight range, and those of protic acids generally in a higher percent by weight range. Preference is given to using 0.01 to 50% by weight of Lewis acid or 0.5 to 80% by weight of protic acid, particular preference to using 0.1 to 30% by weight of Lewis acid or 1 to 50% by weight of protic acid. Examples of suitable solvents in the process according to the invention when using Lewis acids as catalysts include halogenated aliphatic hydrocarbons, for example methylene chloride or chloroform, and when using protic acids as catalysts, depending on the solubility of the protic acid, likewise halogenated aliphatic hydrocarbons or alcohols, for example methanol, ethanol or n-butanol, or else aromatics, for example toluene, xylene or chlorobenzene. It is also possible, for example when reacting liquid thiophene monomers of the general formula II, to carry out the process according to the invention without any solvent.

For the purposes of the present invention, reaction refers hereinabove and hereinbelow to the reaction according to the invention of the compounds of the general formula II with each other in the presence of a Lewis acid and/or protic acid as catalyst to give the compounds of the general formula I according to the invention.

The reaction to give the compounds of the general formula I according to the invention may be carried out at various temperatures, and the yields may depend upon the temperature to a different extent depending the thiophene monomers of the general formula II to be reacted. In general, the reaction is carried out at temperatures of −30° C. to 100° C., preferably −5 to 60° C., more preferably 0° C. to 40° C.

The process according to the invention may be carried out under air or under protective gas, for example nitrogen or argon. Owing to the avoidance of oxidative secondary reactions, preference is given to using protective gas to increase the yields and purities.

The reaction times are dependent upon the temperature and the compound of the general formula II to be reacted. Since the reaction to give the compounds according to the invention may, depending on the catalyst used, be an equilibrium reaction, it may be particularly advantageous to follow the proportions of compounds according to the invention present in the reaction mixture by a suitable analytic method, for example $^1H$ NMR spectroscopy, and to terminate the reaction at an advantageous time. The reaction may be terminated, for example, by adding bases, preferably aqueous $Na_2CO_3$ solution, or termination may be brought about by adding alcohols, preferably ethanol, and, subsequently or at the same time, adding water, or by only adding water.

Examples of monomeric compounds of the general formula II which can be converted to the compounds of the general formula I-a according to the invention are given in the following:

2,3-dihydrothieno[3,4-b][1,4]dioxin (referred to hereinbelow as EDT or ethylene-3,4-dioxythiophene, compound II-a), 2-methyl-2,3-dihydrothieno[3,4-b][1,4]dioxin (2-methyl-EDT, compound II-b where R=methyl and x=1), 2-ethyl-2,3-dihydrothieno[3,4-b][1,4]dioxin (2-ethyl-EDT, compound II-b where R=ethyl and x=1), 2-n-propyl-2,3-dihydrothieno[3,4-b][1,4]dioxin (2-n-propyl-EDT, compound II-b where R=n-propyl and x=1), 2-n-butyl-2,3-dihydrothieno[3,4-b][1,4]dioxin (2-n-butyl-EDT, compound II-b where R=n-butyl and x=1), 2-n-pentyl-2,3-dihydrothieno[3,4-b][1,4]dioxin (2-n-pentyl-EDT, compound II-b where R=n-pentyl and x=1), 2-n-hexyl-2,3-dihydrothieno[3,4-b][1,4]dioxin (2-n-hexyl-EDT, compound II-b where R=n-hexyl and x=1), 2-n-heptyl-2,3-dihydrothieno[3,4-b][1,4]dioxin (2-n-heptyl-EDT, compound II-b where R=n-heptyl and x=1), 2-n-octyl-2,3-dihydrothieno[3,4-b][1,4]dioxin (2-n-octyl-EDT, compound II-b where R=n-octyl and x=1), 2-(2-ethylhexyl)-2,3-dihydrothieno[3,4-b][1,4]dioxin (2-(2-ethylhexyl)-EDT, compound II-b where R=2-ethylhexyl and x=1), 2-n-nonyl-2,3-dihydrothieno[3,4-b][1,4]dioxin (2-n-nonyl-EDT, compound II-b where R=n-nonyl and x=1), 2-n-tetradecyl-2,3-dihydrothieno[3,4-b][1,4]dioxin (2-tetradecyl-EDT, compound II-b where R=n-tetradecyl and x=1), 2,3-dihydrothieno[3,4-b][1,4]dioxin-2-ylmethanol (compound II-b where R=$CH_2OH$ and x=1).

Preferred examples from this group are 2,3-dihydrothieno[3,4-b][1,4]dioxin (EDT), 2-methyl-2,3-dihydrothieno[3,4-b][1,4]dioxin (2-methyl-EDT) and 2,3-dihydrothieno[3,4-b][1,4]dioxin-2-ylmethanol.

A particularly preferred example from this group is 2,3-dihydrothieno[3,4-b][1,4]dioxin (EDT).

Examples of monomeric compounds of the general formula II which can be converted to the compounds of the general formula I-b according to the invention are given in the following:

3,4-dihydro-2H-thieno[3,4-b][1,4]dioxepin (propylene-3,4-dioxythiophene, PDT, compound II-c), 3-methyl-3,4-dihydro-2H-thieno[3,4-b][1,4]dioxepin (3-methyl-PDT, compound II-d where R=methyl and x=1), 3,3-dimethyl-3,4-dihydro-2H-thieno[3,4-b][1,4]dioxepin (3,3-dimethyl-PDT, compound II-d where R=methyl and x=2), 2-methyl-3,4-dihydro-2H-thieno[3,4-b][1,4]dioxepin (2-methyl-PDT, compound II-d where R=methyl and x=1), 3,4-dihydro-2H-thieno[3,4-b][1,4]dioxepin-3-ol, (compound II-d where R=OH and x=1).

Preferred examples from this group are 3,4-dihydro-2H-thieno[3,4-b][1,4]-dioxepin (PDT) and 3,4-dihydro-2H-thieno[3,4-b][1,4]dioxepin-3-ol.

All compounds specified may also be used in a mixture with one another, which may equally result in mixtures of different dimers and trimers or mixed dimers and trimers of different monomers or else mixtures of both types of compound (i.e. those having uniform monomers and those composed of different monomers).

The preparation of the novel compounds according to the invention and the process according to the invention for their preparation is extremely surprising, particularly since it is stated in A. K. Mohanakrishnan, A. Hucke, M. A. Lyon, M. V. Lakshmikantham and M. P. Cava, Tetrahedron 55 (1999), p. 11745–11754 that, for example, ethylene-3,4-dioxythiophene (EDT, compound II-a) enters into extensive decomposition reactions under strongly acidic conditions or in the presence of Lewis acids.

The compounds of the general formula I according to the invention may be oxidatively converted to polythiophenes by chemical or electrochemical means. Useful chemical oxidizing agents are those known from the prior art for polythiophene preparation, for example iron-III compounds such as $FeCl_3$ or iron-III tosylate, potassium permanganate or $MnO_2$, potassium (di)chromate, or peroxodisulphate (persulphate) such as $Na_2S_2O_8$ or $K_2S_2O_8$, or else $H_2O_2$.

The invention thus further provides the use of the compounds of the general formula I according to the invention for preparing neutral or cationic polythiophenes.

The polythiophenes may already be semiconducting to highly conducting as a consequence of the preparative process, or else gain these properties by subsequent oxidation. For the purposes of the invention, semiconducting refers to those polythiophenes which have a conductivity of less than 10 S/cm, and conducting to highly conducting to those having a conductivity of equal to or greater than 10 S/cm, although this boundary may also be shifted upwards or downwards depending upon the substitution pattern of the repeating thiophene units, i.e. depending on the definitions of A, R and x.

The present invention therefore further provides a process for preparing neutral or cationic polythiophenes of the general formula III

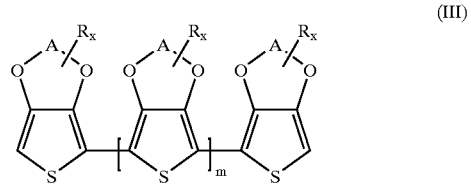

(III)

where

A, R and x are each as defined above for the general formula I and m is an integer from 2 to 200, characterized in that compounds of the general formula I are oxidatively polymerized by chemical or electrochemical means.

For the purposes of the invention, the term polythiophenes also encompasses oligothiophenes, so that polythiophenes encompass all compounds of the general formula III for which m is at least 2 and at most 200.

The polythiophenes of the general formula III may be neutral or cationic. When the polythiophenes are cationic, the positive charges of the polythiophene polycations are not shown in the formula III, since their exact number and position cannot be determined unambiguously. However, the number of positive charges is at least 1 and at most m+2.

To compensate the positive charge, the cationic form of the polythiophenes contains anions, preferably polyanions, as counterions.

The polyanions used are preferably the anions of polymeric carboxylic acids such as polyacrylic acids, polymethacrylic acids or polymaleic acids, and polymeric sulphonic acids such as polystyrenesulphonic acids and polyvinylsulphonic acids. These polycarboxylic and polysulphonic acids may also be copolymers of vinylcarboxylic and vinylsulphonic acids with other polymerizable monomers, such as acrylic esters or styrene.

Particular preference is given to using the anion of polystyrenesulphonic acid as the counterion.

The molecular weight of the polyacids delivering the polyanions is preferably 1000 to 2 000 000, more preferably 2000 to 500,000. The polyacids or their alkali metal salts are commercially available, for example polystyrenesulphonic acids and polyacrylic acids.

Owing to the high reactivity of the compounds according to the invention, the oxidative polymerization proceeds particularly easily and rapidly, which is advantageous over the oxidative polymerization processes of other monomers known from the prior art.

The compounds of the general formula I according to the invention and also the neutral and/or cationic polythiophenes prepared from them may serve to produce organic, electrical or electronic components, for example to produce light elements, photocells or organic transistors, for modifying plastic films for packaging electronic components and for clean-room packaging, antistatic modification of cathode ray tubes, antistatic modification of photographic films, as transparent heating, as transparent electrodes, as circuit boards or for window panes which can be coloured electrically. Oxidative polymerization allows, for example, conductive layers to be generated on non-conducting substrates such as glass, ceramic, plastic, etc. In capacitors, the layers generated in this way may assume the role of the cathode.

The compounds of the general formula I according to the invention may be applied to the substrates in a mixture with the oxidizing agent of organic solvents, for example alcohols, methylene chloride, chloroform, N-methylpyrrolidone, etc., by knife coating, spin coating, pouring, impregnation, etc.

The compounds of the general formula I according to the invention and prepared by the process according to the invention are often light yellowish oils or beige solids which are soluble in organic solvents such as methylene chloride, chloroform or tetrahydrofuran. They can therefore be easily processed from organic solution for applications, for example, in the electronics industry. It is possible to prepare cationic polythiophenes or polythiophene layers having excellent conductivity from such solutions in the presence of a counterion, i.e. even using mild oxidizing agents.

The invention therefore further provides the use of the compounds of the general formula I for producing parts of electrical or electronic components.

Also according to the invention is the use of the compounds of the general formula III which have been prepared from the compounds of the general formula I according to the invention by the abovementioned oxidative polymerization process as a part of electrical and electronic components, in particular as cathodes in capacitors. For example, they may be used as cathodes in capacitors which contain anodes made of valve metals, for example aluminium, niobium, tantalum or alloys thereof.

EXAMPLES

The reactants used hereinbelow (EDT and alkyl-substituted EDT derivatives) are either commercially available or may be prepared by transetherifying the corresponding 3,4-dialkoxythiophenes (for example 3,4-di-n-propoxythiophene), which are easily obtainable by known processes, with vicinal 1,2-diols.

General Method for Synthesizing the Alkyl-Substituted EDT Derivatives:

For example, the alkyl-substituted EDT derivatives may be synthesized by transetherification in such a way that 3,4-di-n-propoxythiophene and a geminal 1,2-diol in a 1:2 molar ratio (100% excess of the diol) are heated to reflux under $N_2$ in toluene with p-toluenesulphonic acid as the catalyst for 2 h, then toluene/n-propanol are gradually distilled off and continuously replaced by xylene. The reaction is continued until such time as the xylene distilled off contains no more n-propanol (monitoring, for example, via the refractive index) or no more 3,4-di-n-propoxythiophene can be detected by thin layer chromatography. If desired, the xylene distilled off is continuously replaced by fresh xylene. After the solution is cooled, it is washed to neutrality with water, dried over $Na_2SO_4$ and chromatographed on a silica gel column using toluene/n-hexane (1:1). After removing the solvent, the alkyl-substituted EDT derivative is obtained.

Example 1

Preparation of 2,2',3,3',5,7-hexahydro-5,5'-bithieno[3,4-b][1,4]dioxin (I-a-1a, EDT Dimer) and 2,2',2'',3,3',3'',5,5'',7,7''-decahydro-5,5':7',5''-terthieno[3,4-b][1,4]dioxin (I-a-1b, EDT Trimer) Using $BF_3$ as the Catalyst 2 ml of a solution of 0.04 ml of $BF_3$ etherate in 20 ml of methylene chloride (corresponding to 0.036 mmol of $BF_3$ or 1.8% by weight of boron trifluoride etherate, based on EDT), are added at 0° C. to a solution of 0.284 g (2 mmol) of 2,3-dihydrothieno[3,4-b][1,4]dioxin (ethylene-3,4-dioxythiophene or EDT; Baytron® M, H. C. Starck GmbH) in 1.5 ml of methylene chloride. The reaction mixture was stirred under an argon atmosphere at 0° C. for 4 h. The reaction was then stopped by adding 2 ml of ethanol and then 4 ml of water. The organic phase was removed and freed of solvent on a rotary evaporator at 20 mbar. The residue was separated by column chromatography on silica gel using methylene chloride as the eluent.

Fraction 1: 0.128 g of EDT (45.5% of the reactant used)

Fraction 2: 0.045 g (16% of theory) of 2,2',3,3',5,7-hexahydro-5,5'-bithieno[3,4-b][1,4]dioxin (EDT dimer) as racemate.

Elemental analysis: Calc: C, 50.69%; H, 4.25%; S, 22.55% ($C_{12}H_{12}O_4S_2$). Found: C, 50.49%; H, 4.45%; S, 22.59%.

Mass spectrum (70 eV); m/z, (rel. intensity): 284 (100.0%), $M^+$; 251 (66.7%); 223 (11.0%); 195 (27.9%); 186 (18.4%); 185 (15.0%); 168 (11.7%); 155 (15.4%); 154 (19.2%); 143 (4.0%), EDT-$H^+$; 142 (14.9%), $EDT^+$ $^1$H NMR (CDCl$_3$, δ in ppm, J in Hz):δ: 3.60 (dd, 1H,$^2$J=11.93, $^5$J=1.96); 3.80 (dd, 1H, $^2$J=11.93, $^5$J=5.48); 4.08 (m, 4H); 4.18 (m, 4H); 5.44 (dd, 1H, $^5$J=1.96, $^5$'J=5.48); 6.26 (s, 1H);

$^{13}$C{$^1$H}NMR (C$_6$D$_6$, δ in ppm):δ: 30.54; 42.42; 64.28; 64.39; 98.27; 120.58; 129.89; 130.68; 139.69; 141.70.

Fraction 3: 0.018 g (6% of theory) of 2,2',2'',3,3',3'',5,5'',7,7''-decahydro-5,5':7',5''-terthieno[3,4-b][1,4]dioxin (EDT trimer), stereoisomer mixture.

Mass spectrum (70 eV); m/z, (rel. intensity): 426 (54.8%), $M^+$; 394 (22.2%), $M^+$-S; 393 (22.8%); 284 (88.2%), $M^+$-EDT; 283 (64.4%); 282 (93.5%); 251 (42.0%); 223 (6.9%); 195 (15.7%); 186 (16.4%); 185 (80.6%); 181 (7.1%); 168 (7.6%); 155 (14.0%); 153 (8.9%); 142 (73.8%), $EDT^+$.

$^{13}$C{$^1$H}NMR (C$_6$D$_6$, δ in ppm):δ: 30.53; 30.60; 42.47; 42.53; 64.11; 64.18; 64.20; 64.24; 64.35; 118.93; 119.19; 129.71; 129.79; 130.59; 130.67; 138.04; 139.02.

Recrystallization of fraction 3 from a hexane/diethyl ether/methylene chloride mixture gave 3 mg of the R,S isomer of the EDT trimer:

$^1$H NMR (CDCl$_3$, δ in ppm, J in Hz):δ: 3.59 (dd, 2H, $^2$J=11.94, $^5$J=1.96); 3.77 (dd, 2H, $^2$J=11.94, $^5$'J=5.48); 4.08 (m, 8H), 4.18 (br. s, 4H); 5.43 (dd, 2H, $^5$J=1.96, $^5$'J=5.48).

Evaporation of the mother liquor from this recrystallization gave 14 mg of an enriched sample of the R,R/S,S isomer mixture of the EDT trimer.

$^1$H NMR (CDCl$_3$, δ in ppm, J in Hz) of the main component:δ: 3.58 (dd, 2H, $^2$J=12.08, $^5$J=1.59); 3.78 (dd, 2H, $^2$J=12.00, $^5$'J=5.40); 4.07 (m, 8H), 4.18 (m, 4H); 5.42 (dd, 2H, $^5$J=1.43, $^5$'J=5.40).

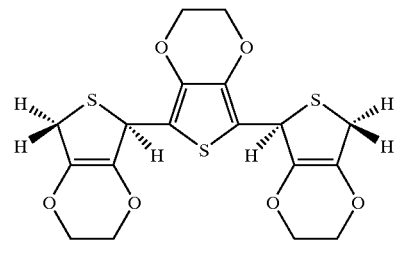

R,S isomer of the EDT trimer

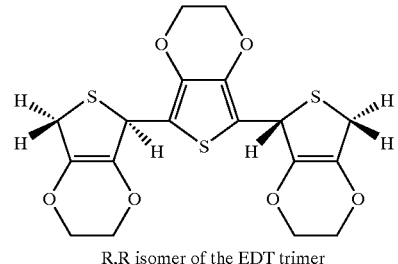

R,R isomer of the EDT trimer

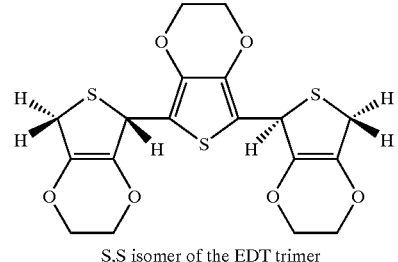

S,S isomer of the EDT trimer

Example 2

Preparation of EDT Dimer and EDT Trimer Using Trifluoroacetic Acid as the Catalyst 0.426 g of trifluoroacetic acid in 18 ml of methylene chloride is added at 18° C. to a solution of 8.52 g (0.06 mol) of ethylene-3,4-dioxythiophene (EDT) in 13.5 ml of methylene chloride. The reaction mixture was stirred under an $N_2$ atmosphere at 18° C. for 48 h. Afterwards, the reaction was stopped by intensive stirring with 30 ml of 5% aqueous $Na_2CO_3$ solution. The organic phase was removed, washed to neutrality with water and freed of solvent on a rotary evaporator at 20 mbar. The residue (8.45 g) was chromatographed on a silica gel column using methylene chloride as the eluent.

Fraction 1: 4.21 g of EDT (49.4% of the reactant used)

Fraction 2: 2.22 g (26.1% of theory) of EDT dimer, identified by means of $^1$H NMR in CDCl$_3$. The spectrum is identical to that described in Example 1. Beige crystals, m.p. 115–119° C.

Fraction 3: 1.0 g (11.7% of theory) of EDT trimer as an isomer mixture, identified by means of $^1$HNMR in CDCl$_3$. The spectrum corresponds to a superimposition of the data reported in Example 1 for the R,S and R,R/S,S isomers. Beige crystals.

Example 3

Preparation of EDT Dimer and EDT Trimer Using TiCl$_4$ as Catalyst 0.426 g of titanium tetrachloride in 18 ml of methylene chloride was added at 20° C. to a solution of 8.52 g (0.06 mol) of ethylene-3,4-dioxythiophene (EDT) in 13.5 ml of methylene chloride. The reaction mixture was stirred under an N$_2$ atmosphere at 20° C. for 8 h. Afterwards, the reaction was stopped by intensive stirring with 30 ml of 5% aqueous Na$_2$CO$_3$ solution. The organic phase was diluted with 20 ml of methylene chloride and removed, washed to neutrality with water and freed of solvent on a rotary evaporator at 20 mbar. The residue (8.0 g) was separated by column chromatography on silica gel using methylene chloride as the eluent.

Fraction 1: substantially EDT

Fraction 2: 1.37 g (16.1% of theory) of EDT dimer, identified by means of $^1$H NMR in CDCl$_3$. The spectrum is identical to that described in Example 1. Beige crystals, m.p. 113–114° C.

Fraction 3: 0.96 g (11.3% of theory) of EDT trimer as an isomer mixture (small proportion of dimer present), identified by means of $^1$HNMR in CDCl$_3$. The spectrum corresponds to a superimposition of the data reported in Example 1 for the R,S and R,R/S,S isomers. Beige crystals.

Example 4

Preparation of the Compound of the Formula I-a-2a where R=methyl and x=1 (2-methyl-EDT Dimer) and the Compound of the Formula I-a-2b where R= methyl and x=1 (2-methyl-EDT Trimer) Using BF$_3$ as Catalyst 0.12 ml of BF$_3$ etherate in 20 ml of methylene chloride (corresponding to 0.95 mmol of BF$_3$ or 4.3% by weight of BF$_3$ etherate, based on methyl-EDT) was added at 0° C. to a solution of 3.124 g (20 mmol) of 2-methyl-2,3-dihydrothieno[3,4-b][1,4]dioxin (2-methyl-EDT; prepared according to the abovementioned synthetic method) in 15 ml of methylene chloride. The reaction mixture was stirred under an N$_2$ atmosphere at 0 to 2° C. for 4 h. Afterwards, the reaction was stopped by adding 20 ml of ethanol and then 40 ml of water. The organic phase was removed and freed of solvent on a rotary evaporator at 20 mbar. The residue was separated by column chromatography on silica gel using methylene chloride as the eluent.

Fraction 1: 1.34 g of reactant (42.9% of the 2-methyl-EDT used)

Fraction 2: 0.79 g (25.3% of theory) of 2-methyl-EDT dimer, isomer mixture, identified by means of $^1$H NMR:

$^1$H NMR (CDCl$_3$, δ in ppm):δ: 1.25–1.34 (several s, 3H); 3.55–3.80 (m, 2H); 3.8–3.9 (m, 2H); 4.0–4.35 (m, 4H); 5.40–5.47 (m, 1H); 6.24 (several s lying close together, 1H);

Fraction 3: 0.34 g (10.9% of theory) of 2-methyl-EDT trimer, according to $^1$H NMR (CDCl$_3$) contaminated with a little 2-methyl-EDT dimer.

Example 5

Preparation of the Compound of the Formula I-a-2a where R=n-tetradecyl and x=1 (2-tetradecyl-EDT Dimer) and the Compound of the Formula I-a-2b where R=n-tetradecyl and x=1 (2-tetradecyl-EDT Trimer) using BF$_3$ as Catalyst 0.06 ml of BF$_3$ etherate in 20 ml of methylene chloride (corresponding to 0.47 mmol of BF$_3$ or 2.0% by weight of BF$_3$ etherate, based on 2-tetradecyl-EDT) was added at 0° C. to a solution of 3.386 g (10 mmol) of 2-n-tetradecyl-2,3-dihydrothieno[3,4-b][1,4]dioxin (2-n-tetradecyl-EDT; prepared according to the abovementioned synthetic method) in 15 ml of methylene chloride. The reaction mixture was stirred under an N$_2$ atmosphere at 0° C. for 4 h. Afterwards, the reaction was stopped by adding 20 ml of ethanol and then 40 ml of water. The organic phase was removed and freed of solvent on a rotary evaporator at 20 mbar. 3.34 g of residue were obtained which, according to $^1$H NMR (CDCl$_3$), consists of 47.2% by weight of 2-tetradecyl-EDT= reactant, 42.1% by weight of 2-tetradecyl-EDT dimer and 10.7% by weight of 2-tetradecyl-EDT trimer (evaluation of the absorptions at δ=6.20 to 6.24 ppm and 5.37 to 5.5 ppm).

Example 6

Reaction of a Mixture of 80% of 2,3-dihydrothieno [3,4-b][1,4]dioxin-2-ylmethanol and 20% of 3,4-dihydro-2H-thieno[3,4-b][1,4]dioxepin-3-ol in the Presence of BF$_3$ as Catalyst 0.12 ml of BF$_3$ etherate in 60 ml of methylene chloride (corresponding to 0.95 mmol of BF$_3$ or 1.9% by weight of boron trifluoride etherate, based on the thiophene reactant mixture) was added at 0° C. to a solution of 3.444 g (20 mmol) of a mixture of 80% of 2,3-dihydrothieno[3,4-b][1, 4]dioxin-2-ylmethanol and 20% of 3,4-dihydro-2H-thieno [3,4-b][1,4]dioxepin-3-ol (Baytron® M OH trial product CH 8020, H. C. Starck GmbH) in 45 ml of methylene chloride. The reaction mixture was stirred under an N$_2$ atmosphere at 0° C. for 4 h. Afterwards, the reaction was stopped by adding 60 ml of ethanol and then 120 ml of water. The organic phase was removed and freed of solvent on a rotary evaporator at 20 mbar. 3.21 g of residue were obtained which, according to $^1$H NMR (CDCl$_3$) consisted at a rough estimate of about 55% by weight of reactant, 30% by weight of dimers and 15% by weight of trimers (evaluation of the absorptions at δ=6.25 to 6.3 ppm and 5.35 to 5.55 ppm). Owing to the complexity of the spectrum, the structure of individual compounds or adducts cannot be determined. An absorption at 6.52 ppm suggests the presence of a dimeric structure of 3,4-dihydro-2H-thieno[3,4-b] [1,4]dioxepin-3-ol (max. 2% by weight).

Example 7

Preparation of EDT Dimer and EDT Trimer Using p-toluenesulphonic Acid as Catalyst in Ethanol 2 g (14 mmol) of ethylene-3,4-dioxythiophene (EDT) and 1 g of p-toluenesulphonic acid were dissolved in 50 ml of ethanol and stirred under an N$_2$ atmosphere at 20° C. for 10 days. Afterwards, the reaction was stopped by adding 30 ml of 5% aqueous Na$_2$CO$_3$ solution. The solution was extracted using methylene chloride, and the organic phase washed to neutrality with water and freed of solvent on a rotary evaporator at 20 mbar. 1.65 g of residue remained which, according to $^1$H NMR in CDCl$_3$, contained 5.2% by weight of the EDT dimer and a trace of the EDT trimer (NMR spectroscopic data corresponding to the pure compounds in Example 1).

Example 8

Preparation of EDT Dimer and EDT Trimer Using Methanesulphonic Acid as Catalyst 0.426 g of methanesulphonic acid in 180 ml of methylene chloride was added at 20° C. to a solution of 8.52 g (0.06 mol) of ethylene-3,4-dioxythiophene (EDT) in 135 ml of methylene chloride. The reaction mixture was stirred under an N$_2$ atmosphere at 20° C. for 6 h. Afterwards, the reaction was stopped by intensive stirring with 30 ml of 5% aqueous Na$_2$CO$_3$ solution. The organic phase was removed, washed to neutrality with water and freed of solvent on a rotary evaporator at 20 mbar. According to $^1$H NMR in CDCl$_3$, the residue (8.5 g) contained 6.3% by weight of the EDT dimer (NMR spectroscopy data corresponding to the isolated compounds in Example 1).

Example 9

Preparation of the EDT Dimer and the EDT Trimer Using SnCl$_4$ as Catalyst 0.426 g of tin(IV) chloride in 18 ml of methylene chloride was added dropwise within 30 min at 20° C. to a solution of 8.52 g (0.06 mol) of ethylene-3,4-dioxythiophene (EDT) in 13.5 ml methylene chloride. The reaction mixture was stirred under an N$_2$ atmosphere at 20° C. for 6 h. Afterwards, the reaction was stopped by intensive stirring with 30 ml of 5% aqueous Na$_2$CO$_3$ solution. The organic phase was diluted with 20 ml of methylene chloride and removed, washed to neutrality with water and freed of solvent on a rotary evaporator at 20 mbar. According to $^1$H NMR in CDCl$_3$, the residue (6.99 g) consisted of 60.5% by weight of EDT, 34.2% by weight of EDT dimer and 5.3% by weight of EDT trimer (NMR spectroscopy data corresponding to the isolated compounds in Example 1).

Example 10

Preparation of EDT Dimer and EDT Trimer Using SbCl$_5$ as Catalyst 0.296 g of antimony(V) chloride in 18 ml of methylene chloride were added dropwise within 30 min at 20° C. to a solution of 8.52 g (0.06 mol) of ethylene-3,4-dioxythiophene (EDT) in 13.5 ml of methylene chloride. The reaction mixture was stirred under an N$_2$ atmosphere at 20° C. for 8 h. Afterwards, the reaction was stopped by intensive stirring with 30 ml of 5% aqueous Na$_2$CO$_3$ solution. The organic phase was diluted with 20 ml of methylene chloride and removed, washed to neutrality with water and freed of solvent on a rotary evaporator at 20 mbar. According to $^1$H NMR in CDCl$_3$, the residue (8.5 g) consisted of 37.2% by weight of EDT, 49.0% by weight of EDT dimer and 13.8% by weight of EDT trimer (NMR spectroscopy data corresponding to the isolated compounds in Example 1).

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. Compounds represented by general formula (I),

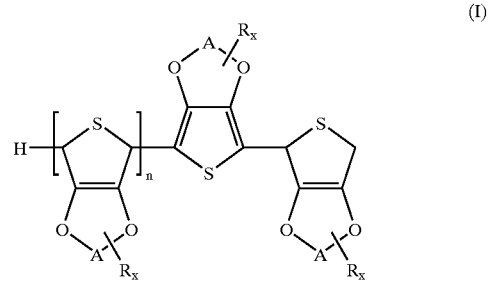

wherein,

A is an optionally substituted C$_1$–C$_4$-alkylene radical,

R is one or more identical or different, linear or branched, optionally substituted C$_1$–C$_{18}$-alkyl radical(s), optionally substituted C$_5$–C$_{12}$-cycloalkyl radical(s), optionally substituted C$_6$–C$_{14}$-aryl radical(s), optionally substituted C$_1$–C$_4$-hydroxyalkyl radical(s) or one or more hydroxyl radical(s), x is an integer from 0 to 8, and n is 0 or 1.

2. The compounds of claim 1, wherein,

A is an optionally substituted C$_2$- or C$_3$-alkylene radical,

R is one or more identical or different, linear or branched, optionally substituted C$_1$–C$_{18}$-alkyl radical(s), optionally substituted C$_5$–C$_{12}$-cycloalkyl radical(s), optionally substituted C$_6$–C$_{14}$-aryl radical(s), optionally substituted C$_1$–C$_4$-hydroxyalkyl radical(s) or a hydroxyl radical, x is an integer from 0 to 6, and n is 0 or 1.

3. The compounds of claim 1, wherein,

A is an optionally substituted C$_2$- or C$_3$-alkylene radical,

R is a linear or branched, optionally substituted C$_1$–C$_{14}$-alkyl radical, an optionally substituted C$_1$–C$_2$-hydroxyalkyl radical or a hydroxyl radical, x is 0 or 1, and n is 0 or 1.

4. The compounds of claim 1, wherein said compounds have a structure selected from the group consisting of general formulae (I-a-1) and (I-b-1),

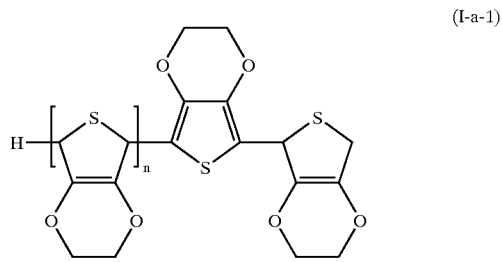

5. A process for preparing compounds represented by general formula (I), (I)

wherein,
A is an optionally substituted $C_1$–$C_4$-alkylene radical,
R is one or more identical or different, linear or branched, optionally substituted $C_1$–$C_{18}$-alkyl radical(s), optionally substituted $C_5$–$C_{12}$-cycloalkyl radical(s), optionally substituted $C_6$–$C_{14}$-aryl radical(s), optionally substituted $C_1$–$C_4$-hydroxyalkyl radical(s) or one or more hydroxyl radical(s),
x is an integer from 0 to 8, and
n is 0 or 1.
said method comprising,
providing compounds represented by general formula (II), (II)

wherein,
A, R and x are each as described for formula (I), and
reacting the compounds represented by formula (II) with each other in the presence of a catalyst selected from the group consisting of Lewis acids, protic acids and combinations thereof.

6. The process of claim 5, wherein said catalyst is selected from non-oxidizing Lewis acids.

7. The process of claim 6, wherein said non-oxidizing Lewis acids are selected from the group consisting of boron trihalides, aluminium trihalides, phosphorus trihalides, titanium tetrahalides, zirconium tetrahalides, tin(IV) halides, arsenic halides, antimony halides, tantalum pentahalides and zinc halides.

8. The process of claim 7, said non-oxidizing Lewis acids are selected from the group consisting of boron trifluoride, antimony pentachloride, titanium tetrachloride and tin tetrachloride.

9. The process of claim 5, wherein said catalyst is a protic acid selected from the group consisting of sulphonic acids, carboxylic acids and superacids.

10. The process of claim 9, wherein said protic acid is selected from the group consisting of p-toluenesulphonic acid, methanesulphonic acid, camphor-10-sulphonic acid and trifluoroacetic acid.

11. A process for preparing a polythiophene comprising polymerizing the compounds of claim 1 represented by general formula (I),
wherein said polythiophene is selected from the group consisting of neutral polythiophenes and cationic polythiophenes.

12. A process for preparing neutral or cationic polythiophenes represented by general formula (III), (III)

wherein,
A is an optionally substituted $C_1$–$C_4$-alkylene radical,
R is one or more identical or different, linear or branched, optionally substituted $C_1$–$C_{18}$-alkyl radical(s), optionally substituted $C_5$–$C_{12}$-cycloalkyl radical(s), optionally substituted $C_6$–$C_{14}$-aryl radical(s), optionally substituted $C_1$–$C_4$-hydroxyalkyl radical(s) or one or more hydroxyl radical(s),
x is an integer from 0 to 8, and
m is an integer from 2 to 200,
said method comprising
(i) providing compounds represented by the following formula (I), (I)

wherein A, R and x are as described for formula (III), and
n is 0 or 1, and
(i) polymerizing the compounds represented by formula (I), wherein the polymerization step is performed by a method selected from the group consisting of chemical polymerization, electrochemical polymerization and oxidative polymerization.

13. A process for producing parts of electrical or electronic components comprising providing the compounds of the general formula (I) according to claim 1.

14. A process for producing a part of an electrical or electronic component comprising providing the compounds of the general formula (III) which have been prepared by the process of claim 12.

15. The process of claim 14 wherein the part is a cathode or a capacitor.

* * * * *